(12) United States Patent
Zhao et al.

(10) Patent No.: US 7,098,309 B2
(45) Date of Patent: Aug. 29, 2006

(54) RECOMBINANT HEPATITIS B SURFACE ANTIGEN

(75) Inventors: Qinjian Zhao, Ambler, PA (US); Robert Sitrin, Lafeyette Hill, PA (US); Dicky G. Abraham, North Wales, PA (US); David P. Gervais, Harleysville, PA (US); Juan Gimenez, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 682 days.

(21) Appl. No.: 09/469,485

(22) Filed: Dec. 22, 1999

(65) Prior Publication Data

US 2003/0113342 A1 Jun. 19, 2003

(51) Int. Cl.
*A61K 38/00* (2006.01)
*C07K 1/00* (2006.01)

(52) U.S. Cl. ...................... 530/333; 530/344

(58) Field of Classification Search ............. 424/199.1, 424/204.1, 207.1; 530/228, 233, 412, 506; 435/5, 41, 69.3
See application file for complete search history.

(56) References Cited

U.S. PATENT DOCUMENTS 4,620,948 A * 11/1986 Builder et al. .............. 530/419
4,707,542 A 11/1987 Friedman et al.
5,242,812 A * 9/1993 Even-Chen ................ 435/70.3

FOREIGN PATENT DOCUMENTS

EP 0314240 3/1989
WO WO 93/24148 * 12/1993

OTHER PUBLICATIONS

Valenzuela et al. Nature. 1979; 280: 815-819.*
Mimms, et al. "Second Generation assays for the detection of antibody to HbsAg using recominant DNA-derived HbsAg". J. Viral Methods 25: 1989, p. 211-232.
Tung, et al. "Characterization of Recombinant Hepatitis B Surface Antigen Using Surface Plasmon Resonance". J. Pharmaceutical Sciences 87: 1998, p. 76-80.
Lohman, et al. "Molecular Characterization and Structural Modeling of Immunoglobin Variable Regions from Murine Monoclonal Antibodies Specific for Hepatitis B Virus Surface Antigen". Molecular Immunol 30: 1993, p. 1295-1306.
Donnelly, JJ., et al. "Adjuvant effects of DNA Vaccines". In VACCINES 97, (Ed. Brown et al., ) 1997, p. 105-111.
Guerrero, et al. "Model for the Protein Arrangement in HBsAg Particles Based on Physical and Chemical Studies" In Viral Hepatitis And Liver Disease (Ed. AJ Zuckerman), p. 606-613.

Hauser, et al., "Inudction of Neutralising Antibodies in Chimpanzees and in Humans by a Recombinant Yeast-Derived Heptaitis B Surface Antigen Particle" In Viral Hepatitis and Liver Disease (Ed. AJ Zuckerman), p. 1031-1037.
Ubuka, T. "Protein Disulfide Isomerase-Catalyzed Renaturation of Ribonuclease A Modified By S-Thiolation With Glutathione and Cysteine". Biochem Mol Biol Int. 38(6): 1996, p. 1103-10.
Valenzuela, P., et al. "Synthesis and assembly of hepatitis B virus surface antigen particles in yeast". NATURE 298: 1982, p. 347-350.
Miyanohara, A., et al. "Expression of hepatitis B surface antigen gene in yeast". PNAS USA 80(1): 1985, p. 1-5.
Wampler, et al. "Multiple chemical forms of hepatitis B surface antigen", Proc. Nat. Acad. Sci. 82: 1985, p. 6830-6834.
Mishiro, S., et al. "A 49,000-Dalton Polypeptide bearing all antigenic determinants and full immunogencity of 22-nm Hepatitis B surface antigen particles". J. IMMUNOLOGY 124: 1980, p. 1589-1593.
Chen, et al. "Discontinous epitopes of hepatitis B surface antigen derived from a filamentous phage peptide library". PNAS 93: 1996, p. 1997-2001.
Musiol, et al. "Redox-active bis-cysteinyl peptides. I. Synthesis of cyclic cysteinyl by conventional methods in solution and on solid supports". BIOPOLYMERS 34: 1994, p. 1553-1562.
Moroder, et al. "Oxidative folding of cysteinerich peptides vs. Regioselective cysteine pairing strategies". BIOPOLYMERS 40: 1996, p. 207-234.
Qiu, et al. "Identification and Characterization of a C(K/R) TC Motif as a Common Epitope Present in All Subtypes of Hepatitis B Surface Antigen". J. IMMUNOL 156: 1996, p. 3350-3356.
Fahey, R.C., "Biologically Important Thiol-Disfulfide Reactions and The Role of Cyst(E)ine in Proteins: An Evolutionary Perspective" University of California, 1977, pp. 1-30.
Lyles, M.M., et al., "Catalysis of the Oxidative Folding of Ribonuclease A by Protein Disulfide Isomerase: Dependence of the Rate on the Composition of the Redox Buffer" BIOCHEMISTRY 30, 1991, p. 613-619.
Tleugabulova, D. "Sodium Dodecylsufate Polyacrylamide Gel Electrophoresis of Recombinant Hepatitis B Surface Antigen Particles" Journal of Chromatography B 707 1998, p. 267-273.
Kennedy, R.C. "Idiotype Networks in Hepatitis B Virus Infections" Curr Topics Microbiol. Immunol. 119, 1985, p. 1-13.

(Continued)

*Primary Examiner*—Shanon Foley
(74) *Attorney, Agent, or Firm*—Michael D. Yablonsky; Jack L. Tribble (57) ABSTRACT

The present invention provides an improved rHBsAg that exhibits a higher antigenicity and immunogenicity than that previously known in the art. A method of making the improved rHBsAg is also provided. The improved HBsAg is used to provide vaccines with lower amounts of active ingredient, vaccines with higher immunogenicity and combination vaccines which produce and protective immunization against infection by hepatitis B virus and other infectious agents.

13 Claims, 8 Drawing Sheets

OTHER PUBLICATIONS

Kennedy, R.C. et al., "Characterization of Anti-Hepatitis B Surface Antigen Monoclonal Antibodies" INTERVIROLOGY 19, 1982, p. 176-180.

Antoni, B. A. et al., "Disulfide Bond Analysis in Hepatitis B Surface Antigen by Mutagenesis of Cyseine esidues Within The Major Antigenic Determinant Region" FASEB J 2 (5) 1988 Abstract 6020.

DéFlora, S. et al., "Enhanced Metabolic Activation of Chemical hepatocarcinogens in Woodchucks Infected with Hepatitis B Virus" CARGINOGENESIS 1989 10(6), p. 1099-106.

Bruce, S. A. et al., "Mutations of Some Critical Amino Acid Residues in the Hepatitis B Virus Surface Antigen" Journal of Medical Virology 46:157 1995 p. 157-161.

Ashton-Rickardt, P. G. et al., "Mutants of the Hepatitis B Virus Surface Antigen That Define Some Antigenically Essential Residues in the Immunodominant a Region" Journal of Medical Virology 29 1989, p. 196-203.

Dreesman, G. R., et al., "Synthetic Hepatitis B Surface Antigen Peptide Vaccine" Adv Exp Med Biol. 185, 1985, p. 129-137.

Luengrojanakul, P. et al., "Common and Subtypic Determinants of Hepatitis B Surface Antigen Particles: Susceptibility to Reduction and/or Alkylation Evaluated with Monoclonal Antibioties" Jpn J Exp Med 60 (5), 1990, p. 253-261.

Antoni, B. A. et al., "Site-Directed Mutagenesis of Cysteine Residues of Hepatitis B Surface Antigen Analysis of Two Single Mutants and the Double Mutant" Eur J Biochem 222(1) 1994 p. 121-127.

Zheng, Y. W., et al., "Negative Regulation of Hepatitis B Virus Gene Expression and Replication by Oxidative Stress" J Biol Chem 269(12) 1994 p. 8857-8862.

Antoni, B. A. et al. "Site Directed Mutagenesis of the Hepatitis B Surface Antigen Gene Creation of a Free-Sulfhydryl Group and Modification of the Protein in the 22NM Particle Structure" J Med Virol 21(4) 1987 Abstract 150.

Mangold, C. M. et al., "Secretion and Antigenicity of Hepatitis B Virus Small Envelope Proteins Lacking Cysteines in the Major Angtigenic Region" VIROLOGY 211(2) p. 535-543.

Fernandes, C. L. et al., "Elevations of Hepatic Quinone Reductase, . . . Isoforms in Mice With Chronic Hepatitis: A Compensatory Response to Injury" Arch Biochem Biophys 331(1) 1996 p. 104-116.

Diminsky, D. et al., "Comparison Between Hepatitis B Surface Antigen . . . Composition, Structure and Immunogenicity" VACCINE 15(6-7) 1997, p. 637-647.

Altomare, E. et al., "Hepatic Glutathione Content in Patients With Alcoholic and Non Alcoholic LIver Disease" Life Sci 43(12) 1988, p. 991-998.

Ionescu-Matiu, I, et al., "Epitopes Associated With A Synthetic Hepatitis B Surface Antigen Peptide" J. Immunol. 130 1983 p. 1947-1952.

Yamamoto, K. et al., "Naturally Ocurring Escape Mutants of Hepatitis B Virus with Various Mutations in the S Gene in Carriers Seropositive for Antibody to Hepatitis B Surface Antigen" J Virol. 68(4) 1994 p. 2671-6.

Ohnuma, H. et al., "Synthetic Oligopeptides Bearing A Common or Subtypic Determinant of Hepatitis B Surface Antigen" J. Immunol. 145(7) 1990, p. 2265-2271.

Neurath, A. R. et al., "Localization of a Hepatitis B Surface Antigen Determinant Deduced From Results of Chemical Modifications" J. Virol. Methods 3(2) 1981 p. 115-125.

Huovila, A. J. et al., "Hepatitis B Surface Antigen Assembles in a Post-ER, Pre-Golgi Compartment" J. Cell Biol. 118, (6) 1992, p. 1305-1320.

Kennedy, R.C. et al., "Common Idiotypic Determinant Associated with Human Antibodies to Hepatitis B Surface Antigen" J. Immunol. 130 1983 p. 385-389.

Zajac, B.A. et al., "Improvements in the Immunogenicity and Purity of a Genetically Engineered Hepatitis B Vaccine" HEPATOLOGY, vol. 8, No. 5, 1988, Abstract 416.

Manivel, V. et al. " A Synthetic Peptide Spontaneously Self-Assembles to Reconstruct A Group-Specific, Conformational Determinant of Hepatitis BSuface Antigen" J of Immunol. 148 (12) 1992, p. 4006-4011.

* cited by examiner

SCHEMATIC REPRESENTATION FOR EPITOPE EVOLUTION

LATENT EPITOPES → → MATURE EPITOPES

FIG.1A

CHEMICAL CONVERSION – INTERCHAIN DISULFIDE BOND CROSS-LINKING p24   ⟶   (p24)$_2$   ⟶   (p24)$_{3-100}$
FORM I           FORM II          FORM III

V_K GENE REGION SEQUENCE COMPARISONS

A1.2  GACATTGTGCTGACCCAGTCTCCAGCAATCATGTCTGCATCTCCAGGGGAGAAGGTCACCATGACCTGCAGTGCCAGTCAGTCAGTGAGTTACATGTAC***TGGTACCACCAGAAGCCAGGATCCTCCCCCAGACTCCTGATTTTTGACACATCCAACCTGCCTTCCTGGAGTCCCTGTT

A1.2  D  I  V  L  T  Q  S  P  A  I  M  S  A  S  P  G  E  K  V  T  M  T  C  |S  A  S  S  S  V  S  Y  M  Y  *|  W  Y  Q  Q  K  P  G  S  S  P  R  L  L  I  F  |D  T  S  N  L  P  S|  G  V  P  V

CDR 1 — CDR 2 — CDR 3 — Jκ

A1.2  CCCTTCAGTGGCAGTGGGTCTGGGACCTCTTACTCTCTCACAATCAGCCGAATGGAGGCTGAAGATGCTGCCACTTATTACTGCCAGCGGTGGAGTACTTACCCACCCATCACGTTCGGAGGGGGGACCAAACTGGAAATAAAACGGGCTGATGCTGCACCACTGTACCATC

V_H GENE REGION SEQUENCE COMPARISONS OF ANTI-HBS

```
                                                   CDR 1
          10        20        30        40        50        60        70        80        90       100       110                   120       130       140    150      160       170    180
A1.2   GATGTGCATCTTCAGGAGTCAGGACCTGAGCTGGTGAAGCCTGGGGCTTCAGTGAAGATATCCTGCAAGGCTTCTGGCTACTCCTTCATTGACCACTATATAAACTGGGTGAAGCAGAGACCCTGAACAGAAGCCTGGACTGAGTGGATTGGATGATTTTTTCCTGAAGCGGTAATAGTAAGTAC
            1         10        20        30                                                                    40                                    50  52a  55
A1.2   D  V  H  L  Q  E  S  G  P  E  L  V  K  P  G  A  S  V  K  I  S  C  K  A  S  G  Y  S  F  I |D  H  Y  I  N| W  V  K  Q  K  P  G  Q  G  L  E  W  I  G |C  F  F  P  G  S  N  S  K  Y

CDR 3
                                                                                                                     D                          JH
         190       200       210       220       230       240       250       260       270       280       290       300       310       320       330       340       350       360
A1.2   ATTGACAACTTCAGGGGCCAAGCCCACATTGACTGTAGACACATCCTCCAGTACAGCCTACATGCAGCTCAGCAGCCTGACATCTGAGGACACTGCTGTCTATTTCTGTGCAAGGGATGATTCCCACGGA***********+CCTATGGACTACTGGGGTCAAGGAACCTCAGTCACC
         60                                     70                                        80                                      90                                    100                   110                              119
A1.2   I  E  N  F  R  G |K  A  T  L  T  V  D  T  I  S  S  S  T  A  Y  M  Q  L  S  S  L  T  S  E  D  T  A  V  Y  F  C  A  R |D  D  S  D  G  *  *  *  *  A  M  D  Y| W  G  Q  G  T  S  V  T
```

FIG.3B

DAY 1          PRE-TREAT STANDARD AND SAMPLES - SECTION III.A.

DISPENSE 200 mcL OF EACH TREATED STANDARD
OR SAMPLE DILUTION INTO WELLS
↓
DISPENSE 200 mcL OF THE DILUENT CONTROL AND
THE KIT CONTROLS INTO REPLICATE WELLS
↓
ADD 50 mcL OF CONJUGATE TO WELLS
↓
TAP TRAY GENTLY TO MIX
↓
ADD ONE BEAD TO EACH TEST WELL
↓
INCUBATE TRAYS FOR 12-20 HOURS AT 20-28°C
↓

DAY 2     WASH BEADS 1 CYCLE WITH 14 ± 3 mL DISTILLED WATER
↓
TRANSFER BEADS TO TUBES
↓
ADD 300 mcL OF OPD SUBSTRATE SOLUTION
↓
INCUBATE 30 TO 35 MINUTES AT 20-28°C IN THE DARK
↓
ADD 1 mL OF 1N SULFURIC ACID TO EACH TUBE
↓
READ TUBES IN QUANTUMATIC™ WITHIN 2 HOURS

-READ KIT CONTROLS BLANKED ON SUBSTRATE

-READ STANDARDS AND TEST BLANKED ON SAMPLE DILUENT.

SEQUENCE LISTING

```
<160> NUMBER OF SEQ ID NOS: 4

<210> SEQ ID NO 1
<211> LENGTH: 4
<212> TYPE: PRT
<213> ORGANISM: Hepatitis B
<220> FEATURE:
<221> NAME/KEY: VARIANT
<222> LOCATION: (1)...(4)
<223> OTHER INFORMATION: Xaa = Any Amino Acid

<400> SEQUENCE: 1

Cys Xaa Tyr Cys
1

<210> SEQ ID NO 2
<211> LENGTH: 4
<212> TYPE: PRT
<213> ORGANISM: Hepatitis B

<400> SEQUENCE: 2

Cys Lys Thr Cys
1

<210> SEQ ID NO 3
```

```
<211> LENGTH: 351
<212> TYPE: DNA
<213> ORGANISM: Mouse

<400> SEQUENCE: 3
gacattgtgc tgacccagtc tccagcaatc atgtctgcat ctccagggga gaaggtcacc      60
atgacctgca gtgccagctc aagtgtaagt tacatgtact ggtaccagca gaagccagga     120
tcctccccca gactcctgat ttttgacaca tccaacctgc cttctggagt ccctgttcgc     180
ttcagtggca gtgggtctgg gacctcttac tctctcacaa tcagccgaat ggaggctgaa     240
gatgctgcca cttattactg ccagcggtgg agtacttacc cacccatcac gttcggaggg     300
gggaccaaac tggaaataaa acgggctgat gctgcaccaa ctgtatccat c              351

<210> SEQ ID NO 4
<211> LENGTH: 345
<212> TYPE: DNA
<213> ORGANISM: Mouse

<400> SEQUENCE: 4
gatgtgcatc ttcaggagtc gggacctgag ctggtgaagc ctggggcttc agtgaagata      60
tcctgcaagg cttctggcta ctccttcatt gaccactata aaactgggt gaagcagaag      120 cctggacagg gacttgagtg gattggatgc ttttttcctg gaagcggtaa tagtaagtac     180
attgagaact tcagggcaa ggccacattg actgtagaca catcctccag tacagcctac      240
atgcagctca gcagcctgac atctgaggac actgctgtct atttctgtgc aagggatgat     300
tccgacggag ctatggacta ctggggtcaa ggaacctcag tcacc                     345
```

RECOMBINANT HEPATITIS B SURFACE ANTIGEN

CROSS-REFERENCE TO RELATED APPLICATIONS

Not applicable

STATEMENT REGARDING FEDERALLY-SPONSORED R&D

Not applicable

REFERENCE TO MICROFICHE APPENDIX

Not applicable

FIELD OF THE INVENTION

The invention relates to recombinant hepatitis B surface antigen (rHBsAg), prophylactic and therapeutic vaccines containing HBsAg and methods of preparing HBsAg and vaccines.

BACKGROUND OF THE INVENTION

The major surface antigen of the hepatitis B virus is a 25 kDa protein, HBsAg. The protein is known in three forms: preS1, preS2 and S. The preS1 and preS2 forms include 14 and 39 amino acids that are cleaved from their N-termini in vivo to yield the 226 amino acid S form. (Valenzuela P., et al. (1979) Nature, 280:815; Valenzuela P., et al., Synthesis and assembly of hepatitis B virus surface antigen particles in yeast. Nature. (1982) 298:347–350. Miyanohara A., et al., Expression of hepatitis B surface antigen gene in yeast. PNAS U S A (1983) 80(1):1–5)

Over the past two decades, recombinant hepatitis B surface antigen expressed as the S form in yeast cells (rHBsAg) has superseded plasma-derived antigen as a vaccine against hepatitis B infection (Valenzuela et al., 1982; McAleer et al., 1984). In the plasma of infected animals, the surface antigen protein assembles into 22 nm particles comprising lipids and HBsAg. However, the assembly of the yeast produced rHBsAg into these virus-like particles has remained poorly understood.

It has been established that reduction of the disulfide bonds in HBsAg abolishes or greatly decreases both its antigenic and immunogenic properties (Reviewed by Tiollais et al., 1981, Guesser et al., 1988; Mishiro et al., 1980; Chen et al, 1996; Hauser, et al 1988). For example, eleven out of the total 14 cysteine residues are conserved among three different type of S protein of Hepatitis B viruses, namely, HBsAg of human, woodchuck, and ground squirrel viruses. However, these three types of S protein share only medium to low overall sequence homology among (Stirk et al, 1992). Interestingly, all 8 cysteine residues in the "a" determinant loop (62 aa between predicted Helix B and Helix C) are fully conserved. This indicates that disulfide bonds may have an important role in maintaining the structural integrity of the antigenic determinants or epitopes (Stirk et al., 1992).

The importance of the presence of disulfide bonds to the functional and structural integrity of proteins has been well documented, particularly for ribonuclease A (Ubuka T., (1996) Protein disulfide isomerase-catalyzed renaturation of ribonuclease A modified by S-thiolated with glutathione and cysteine. Biochem Mol Biol Int. 38(6):1103–10; Fahey, R. C., (1977) Biologically important thiol-disulfide reactions and the role of cyst(e)ine in proteins: an evolutionary perspective. Adv Exp Med Biol. 86A:1–30; Lyles M M, et al., (1991) Catalysis of the oxidative folding of ribonuclease A by protein disulfide isomerase: dependence of the rate on the composition of the redox buffer. Biochemistry. 22;30(3):613–9).

In the case of rHBsAg, the correct disulfide bond pairings are important antigenic determining factors since they are most likely required for the integrity and stability of the major epitopes. (Wampler et al., 1985). Multiple chemical forms of hepatitis B surface antigen. Proc. Nat. Acad Sci. 82:6830–6834. On over-expression in yeast cells, it is believed that the HBsAg molecules need to find a lipid environment for folding into the membrane-embedded structures as seen in the plasma-derived 22 nm lipid/protein particles. However, because of a lack of the control of the cellular redox environments, unlike the propagation of the virus in the infected cells, during over-expression, and sub-optimal conditions during purification and formulation of rHBsAg, the recombinant proteins are expected to assume certain sub-optimal conformations as a result of mismatched disulfide bond pairings.

Although some cysteine-rich proteins or peptides are reported to have strong propensity to form the correct disulfide bond pairings during oxidative refolding (Moroder et al., 1996; Mosiol et al., 1994), productive folding is always in competition with nonproductive folding. These latter pathways lead to either wrong disulfide bond pairings or aggregation of polypeptides.

The rate and yield of oxidative renaturation of small reduced polypeptides have been reported to be influenced by the ratio of low molecular weight disulfide/thiol compounds. The relationships are rather complex and do not parallel the redox potential of the system, as reported using reduced RNAse A as a model protein (Wetlaufer et al., 1987).

It is reported that a redox buffer with both forms of glutathione, i.e., GSSG/GSH mixture, might facilitate the conformational searching by promoting the formation of the correct pairings and unlocking the mismatched ones. However, the use of GSSG/GSH mixtures was only demonstrated for some small proteins and peptides (Moroder, et al., 1996).

It is believed that in a natural system of cells infected by HBV, the nascent HBsAg molecules need to find a lipid environment for the formation of certain intramolecular and/or intermolecular disulfide bonds that lead to proper folding into the native conformation of the protein. In the natural system, this process leads to the formation of particles of approximately 22 nm in diameter made up predominantly of HBsAg protein associated with a lipid membrane. Similarly, when expressed in yeast cells or other expression host, it is believed that the nascent rHBsAg needs to find a lipid environment prior to the spontaneous folding into membrane-embedded structures.

However, in recombinant processes, the rHBsAg is over-expressed in a non-natural system using a host cell. Insect, yeast and CHO cells are commonly used although other cell types may be employed. When overproduced in such a system, the rHBsAg is an assortment of aggregations of scrambled forms and non-native conformations due to mismatched disulfide bond pairings. These artifacts of over-expression yield molecules locked into conformations of low antigenicity. Therefore, once produced, the over-expressed rHBsAg is typically processed outside a cellular environment to eliminate some of the undesired artifacts of over-expression.

Figure 1A:
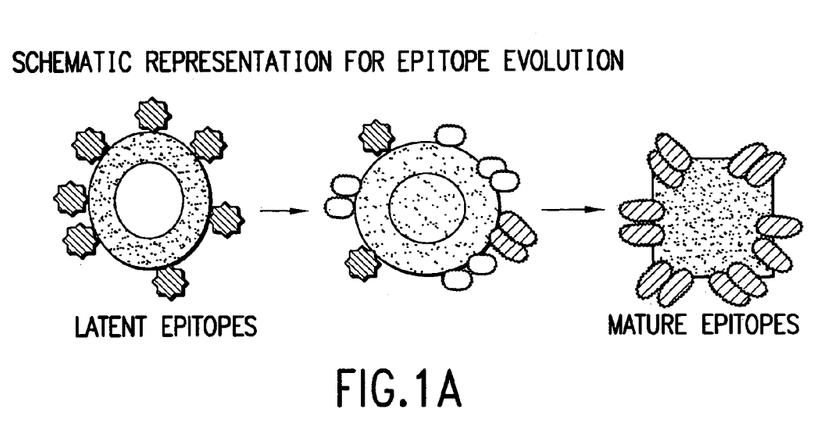
FIG. 1. shows a schematic of the theory of conformational search as applied to rHBsAg.
Figure 1B:
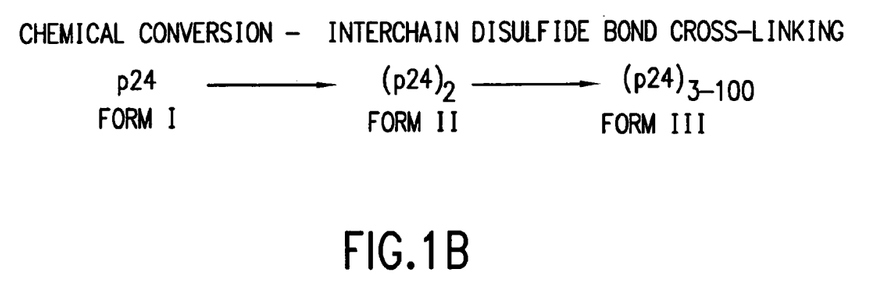

In a method presently used in the art, once the overexpressed rHBsAg is purified from the host cells, the antigen is treated with thiocyanate in an oxidative step to induce a conformational search and yield the form of rHBsAg known as Form III (Wampler, et al., 1985) (See FIG. 1). Thereafter, formalin treatment is used to lock the rHBsAg into whatever conformation it has assumed under the chaotropic, partially denaturing conditions of the thiocyanate treatment. Finally, the rHBsAg it is precipitated with adjuvant.

Previous studies reported that one could achieve an enhancement of antigenicity of rHBsAg by incubation at elevated temperatures as well as the inhibitory effect of formalin to the same process. Moreover, the role of the different disulfides being generated (i.e., intra- and intermolecular) was also described (Wampler, et al., (1985)). In these studies, the conformational search for the thermodynamically most stable forms of rHBsAg occurred spontaneously. Therefore, the optimal percentage of correct three-dimensional structures of the rHBsAg could not be obtained by those methods. Most importantly, the reported procedures yield product that varies for potency as well as consistency. This is possibly due to the poorly-controlled redox conditions, residual metals and surface contacts during process and formulation. Thus, vaccines including rHBsAg made by previously reported methods varies considerably in amount of protein required to induce a protective response in a vaccinated subject.

SUMMARY OF THE INVENTION

The present invention provides an improved recombinant hepatitis B surface antigen, rHBsAg, that has a higher specific antigenicity than previously known rHBsAg. The invention also provides for the use of this improved rHBsAg in prophylactic and therapeutic vaccines and in combination vaccines.

DETAILED DESCRIPTION OF THE INVENTION

The present invention provides an improved recombinant hepatitis B surface antigen protein, "rHBsAg," that exhibits a higher antigenicity than previously known rHBsAg and a method of making the improved rHBsAg. The invention also provides for the use of the improved rHBsAg in prophylactic and therapeutic vaccines, and in combination vaccines.

Briefly, the present invention employs a discovery that an optimized process of refolding rHBsAg can be used to achieve a product having a higher level of immunogenicity than previous rHBsAg products. The immunogenicity is measured by determining the amount of rHBsAg required to induce an immune response in a mouse model system. The optimized process preferably includes a redox buffer step to prepare the improved rHBsAg. It has been discovered that oxidative refolding of rHBsAg in a redox buffer produces a rHBsAg product of higher antigenicity than previously known in the art.

As used herein, antigenicity of rHBsAg refers to the reactivity of the rHBsAg in an in vitro test or system. The immunogenicity of rHBsAg refers to the ability of the rHBsAg to induce an immune reaction in an in vivo animal model or in a patient in a clinical setting.

Without wishing to be bound by any particular theory, it is believed that the use of a redox buffer enables the rHBsAg polypeptides to undergo a conformational search in a more controlled manner over a protracted period of time. The higher immunogenicity of the rHBsAg produced by this process may therefore be due to the preparation of polypeptides having a greater percentage of correct disulfide bond pairings. However, because the rHBsAg protein is a large polypeptide having 14 cysteines and a complex, membrane embedded three dimensional structure, these hypothetical statements may not represent a complete explanation of the factors that lead to the improved immunogenicity of the rHBsAg products taught herein. The interplay between polypeptides in a particle of rHBsAg may also play an important role.

There are approximately 100 rHBsAg polypeptides in a particle. These polypeptides can form dimers and trimers by intermolecular disulfide bonding. The process of making rHBsAg taught herein may produce particles with more, or properly folded, multimers of polypeptides. For example, it is possible that the improved rHBsAg produced as taught herein is due to improved dimerization of the polypeptides in the particles to yield conformations that are more immunogenetic. Therefore, theoretically, it is possible that the improved immunogenicity of the rHBsAg taught herein is due to more proper intra-molecular bonds, inter-molecular bonds, or both.

Redox Buffers in the Folding of rHBsAg

A variety of thiol containing compounds can be used to make a redox buffer for use in the method of making improved rHBsAg. The basic requirements are that the thiol of the compound can interact with cysteine in rHBsAg and that the compound can exist in an oxidized form consisting of a dithiol linkage between two molecules of the compound. Examples of thiol compounds that can be made in reduced and oxidized states are cysteine, 2-mercaptoethanol, thiothreitol, dithiothreitol ("DTT"), glutathione ("GSH") and diglutathione (oxidized glutathione "GSSG"). Our most preferred redox buffer is composed of a mixture of GSH and GSSG due to their abundance in all mammalian cells for redox regulation. It is preferred that one adds the reduced and oxidized compounds (e.g.: GSH/GSSG) at a molar ratio from about 30:1 to about 1:1, preferably, a ratio of about 25:1, 20:1, 10:1, 10:4, 5:1, 2:1 or 1:1, and most preferably at a ratio of about 5:1. The final concentration of the compounds should be between about 0.05 to 5.00 nM, preferably about 0.20 to about 3.0 mM, more preferably about 0.5 to about 1.5 mM, and most preferably about 1.0 mM.

When referring to ratios and concentrations in this specification, we use the term "about" to acknowledge that the invention involves applying reagents to a complex biochemical system. Strict adherence to an absolute, time, concentration or ratio as explicitly recited herein is not frequently required. Moreover, one of skill in the art can use routine empirical testing of ratios and concentrations within 10%, 20% 25% or even 50% of more of the values explicitly stated herein to determine the quality of the product produced by the process when a particular thiol compound is employed in the conformational search step. Similarly, the times required for incubations can vary from those explicitly stated herein.

The appropriateness of any of these variations can be determined routinely by testing the rHBsAg product, (e.g.: using a standard mouse potency assay) to determine whether the variation yields a product having the improved antigenicity produced when using the conditions and reagents explicitly recited herein. Simply stated, this specification teaches that one can in fact produce an improved rHBsAg through the use of a conformational search step in the presence of a redox buffer. Therefore, one who practices in this field can use that teaching to determine the parameters appropriate for employing various particular redox buffers under a variety of conditions to achieve the improved rHBsAg.

Figure 2A:
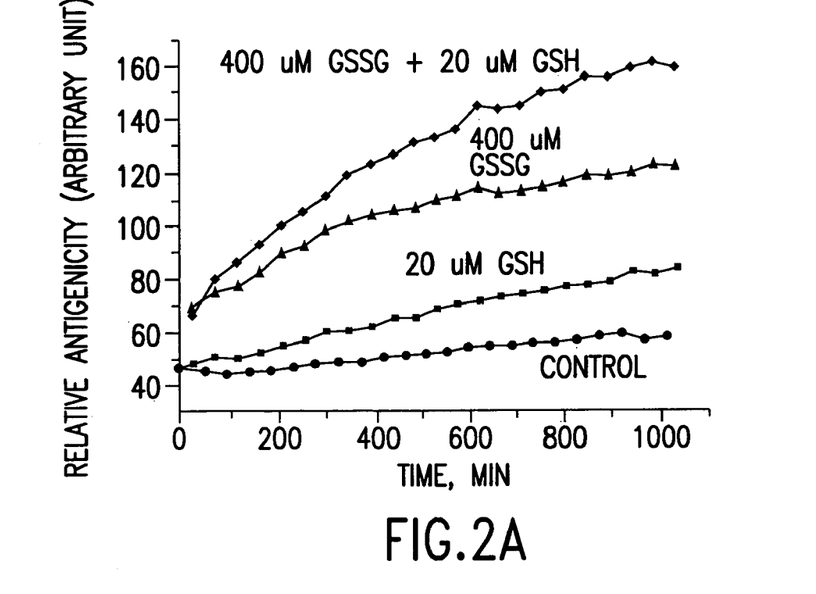
FIG. 2A. Glutathione-mediated conformational search/maturation of rHBsAg at 37° C. Synergistic effects of GSH and GSSG. Measured by surface plasmon resonance in reference to a stable rHBsAg preparation and graphed using arbitrary units.
Figure 2B:
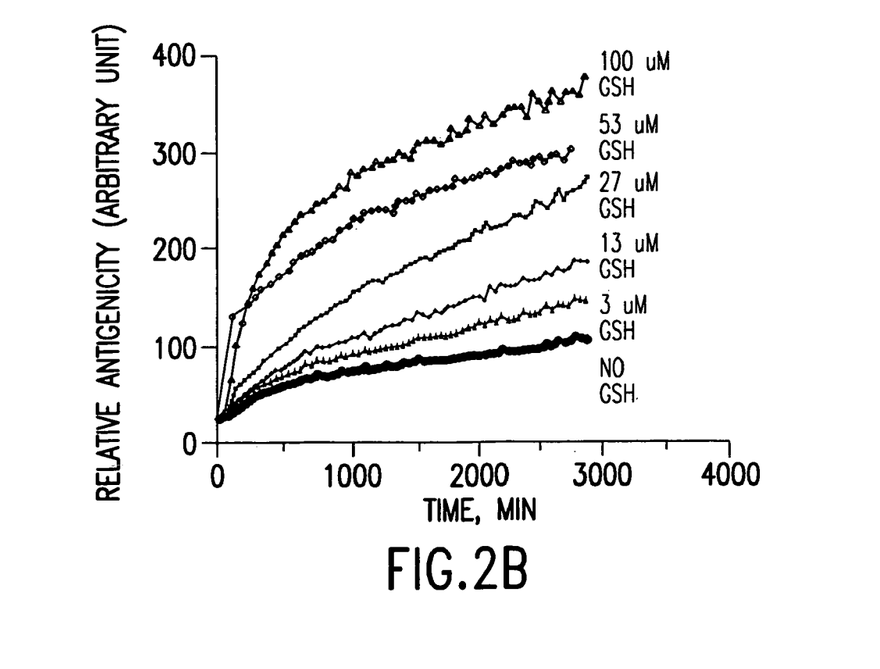
FIG. 2B. Glutathione-mediated conformational search/maturation of rHBsAg at 37° C. A more antigenic conformation of HBsAg can be achieved by higher concentrations of GSH. Measured by surface plasmon resonance in reference to a stable rHBsAg preparation and graphed using arbitrary units.
Figure 3A:
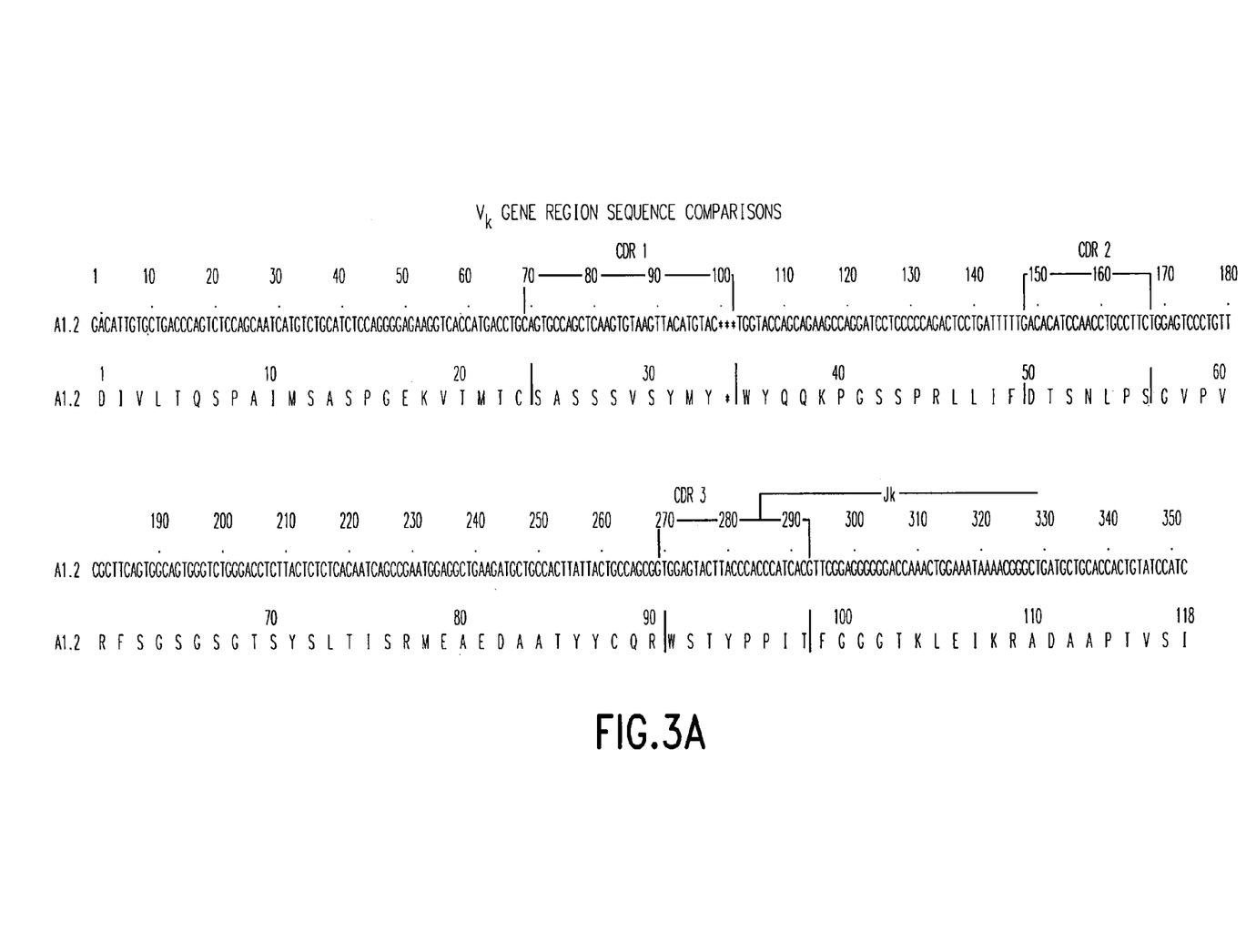
FIG. 3. The nucleotide and protein sequences of the variable regions of the mouse monoclonal antibody A1.2 (from FIGS. 1 and 2 of Lohman et al 1993).
Figure 3B:
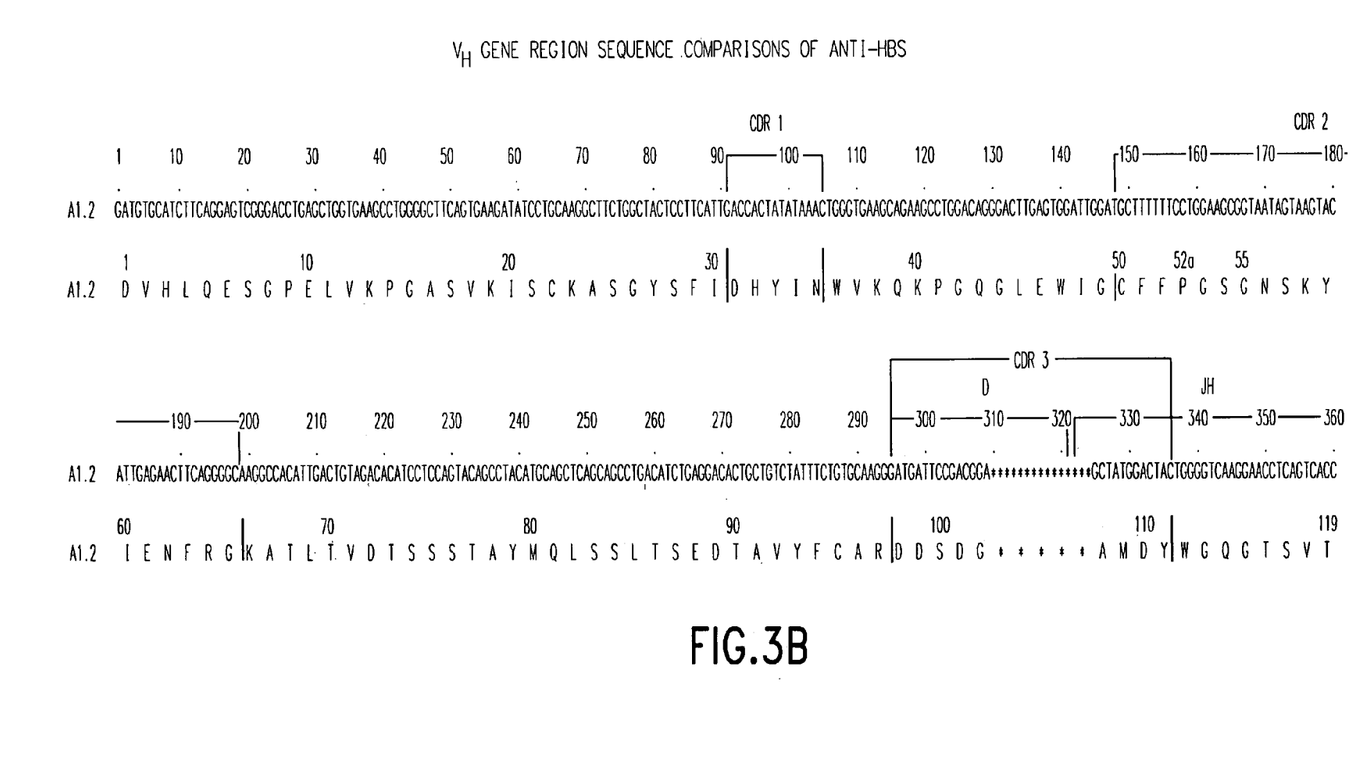

The redox buffer is used to induce what is believed to be a protracted conformational search, especially under warm physiological conditions. The concept of conformational search, i.e., the evolution of the latent epitopes into fully functioning or mature ones through the optimal pathways, and the chemical cross-linking of the rHBsAg polypeptide chains are shown in FIG. 1. Using redox buffer, the rHBsAg molecules are allowed to mature in a state of conformational flux as they search for the thermodynamically most stable conformation. The redox buffer is believed to prevent premature locking of conformation, as well as the covalent disulfide bonding coupled to undesired aggregation. The reducing power of the redox buffer is also believed to unlock the mismatched or scrambled disulfide bonds. These disulfide bonds are much more susceptible to reduction than the correct disulfide pairings. FIGS. 2A and 2B show the dramatic effects of both forms of glutathione on the enhancement of antigenicity of rHBsAg, particularly their synergistic effects in refolding this cysteine-rich protein.

Thus, it is believed that the most advantageous use of the redox step is to use conditions under which the presence of the redox buffer compounds is influential enough to disrupt the less stable mismatched disulfides but not so influential as to constantly disrupt both mismatched and correctly paired disulfide bonds. The preferred and most preferred conditions described herein are appropriate when using GSH/GSSG. However, the conditions appropriate for the use of other thiol compounds can be determined simply by empirical testing of conditions coupled with monitoring of the antigenicity and immunogenicity of the rHBsAg produced.

The redox buffer step is added to existing processes for the production of rHBsAg at the point where the protein is purified from the cellular expression system in which it is produced. For example, using the method of Wampler et al, 1985, the rHBsAg is processed as described up to the point of producing the sterile filtered product, or SFP. SPF should be held at 4° C. until use in the redox step. The SPF is placed in an appropriate vessel such as a glass lined tank. A means of mixing the contents of the tank should be provided. If appropriate, multiple batches of SFP can be combined. If that is the case, we prefer to combine all batches to be treated together in a redox step and to blend them gently and briefly before adding the redox buffer.

The redox step can be performed at a variety of temperatures. The step should be conducted at between 4° C. and 55° C. However, certain considerations lead one to conduct the step at between 18° C. and 45° C. It should be noted that the rHBsAg polypeptides are embedded in a lipid membrane. The fluidity of the membrane should be considered. For example, while one can choose to conduct the step cold temperatures, 4° C. to 10° C., that is not preferred because the thermodynamics of the process would slow to the point where an enormous amount of time would be required to complete the step. At the upper end of the range, higher temperatures lead to more flexibility in the rHBsAg polypeptide and fluidity within the lipids. While that can lead to a faster search, it can also lead to a situation where the correct disulfide bonds are more easily disrupted by attack from the buffer compounds or other cysteines. Additionally, the protein can denature at high temperatures. The temperature should be high enough to allow movement of the polypeptides within the membrane. Therefore, we prefer to use temperatures high enough to produce a result in a reasonable amount of time but not so high as to lead to instability in correctly paired cysteines of protein denaturation. Our preferred temperature ranges are 20° C. to 45° C., more preferably 30° C. to 40° C. and most preferable 34° C. to 38° C. Temperature can be controlled by a variety of means including the use of a jacketed vessel.

We prefer to conduct the redox step without mixing beyond that required to distribute the redox buffer through the batch at the beginning of the step. A dip-tube or other appropriate means of adding the redox buffer can be used with gentle and brief agitation sufficient to distribute the buffer through the batch. Thereafter, the batch is allowed to stand for a period of time.

While the optimal ratio of GSH/GSSG, their concentrations and the duration for incubation might be difficult to predict, routine empirical experiments have shown that the following conditions are preferred: When using a redox buffer of GSH/GSSG with a ratio of 5:1 and a final concentration of 1.0 mM GSH and 0.2 mM GSSG, and our most preferred temperature range of 34° C. to 38° C., we prefer to incubate the mixture for about 20 to 140 hours, more preferably, about 80 to 120 hours and most preferably, about 100 hours. This incubation refers to the time from the beginning of the heating step to the end of the redox buffer incubation step and prior to any formalin treatment that may be desired.

Relevance of Tertiary Structure to Potency.

It is known that the plasma-derived HBsAg is fully cross-linked by disulfide bonds (E. Guesser et al. Model for the protein arrangement in HBsAg Particles based on physical and chemical studies. 1988. In *"Viral Hepatitis and Liver Disease"* pp. 606–613 (ed. A. J. Zuckerman). Alan R. Liss, Inc., New York). It is reported in the literature that the recombinant HBsAg particles are disulfide cross-linked after the downstream purification (Wampler et al. 1985. Multiple chemical forms of hepatitis B surface antigen. *Proc. Nat.*

Acad. Sci. 82:6830–6834). There is also evidence in the literature that mouse immunogenicity of HBsAg resides in the disulfide linkage of two 24 kDa monomeric subunits into a 49 kDa dimer (S. Mishiro et al. 1980. A 49,000-Dalton Polypeptide bearing all antigenic determinants and full immunogenicity of 22-nm Hepatitis B surface antigen particles. *J. Immunology*, 124:1589). Furthermore, a report has contended that MAb RF1, a neutralizing monoclonal antibody that has been shown to protect chimpanzees after viral infection, reacts in Western blots only with oligomeric forms held by disulfides and not with the monomeric 24 kDa subunit (P. Hauser et al. 1988. Induction of neutralizing antibodies in chimpanzees and in humans by a recombinant yeast-derived hepatitis B surface antigen particle. *"Viral Hepatitis and Liver Disease"* pp. 1031–1037 (ed. A. J. Zuckerman). Alan R. Liss, Inc., New York). Finally, Chen et al (1966) have reported monoclonals that bind to epitopes that are believed to be conformational.

These reports support the notion that inter-molecular disulfides are critical for antigenicity and immunogenicity. However, intra-molecular disulfides may also contribute to the product antigenicity. For example, the epitope recognized by monoclonal antibody H166 is reported to be linear (Chen et al., 1996. Discontinuous epitopes of hepatitis B surface antigen derived from a filamentous phage peptide library PNAS 93:1997–2001). However, it is believed that those 4 residues bound by H166 (Cys[121]-Cys[124]) represent a beta turn motif between two alpha-helix regions that is held by an intra-molecular disulfide (Chen et al. 1996 ). In fact, the sequence Cys-X-Y-Cys is contained in the active site of oxidoreductases and their redox potential reflect the propensity of this bis-cysteinyl motif to form disulfide loops (H-J. Musiol et al. 1994. Redox-active bis-cysteinyl peptides. I. Synthesis of cyclic cysteinyl peptides by conventional methods in solution and on solid supports. *Biopolymers*, 34:1553–1562; L. Moroder et al., 1996. Oxidative folding of cysteine-rich peptides vs. Regioselective cysteine pairing strategies. *Biopolymers*, 40:207–234).

Presence of Cys[121]-Cys[124] in rHBsAg.

It is known that in plasma-derived HBsAg is cleaved by trypsin at the carboxyl end of Lys[122] only after reduction of this intramolecular loop (Cys[121]-Cys[124]) with 2-mercaptoethanol. Therefore, the susceptibility of rHBsAg product to the trypsin was tested before and after the KSCN and formulation steps as a measure of proper conformation of the protein. The rationale of the experiment was to determine whether this intramolecular disulfide loop is present in the product before conversion or is generated during the conversion to Form III. The SDS-PAGE analysis of different-step products revealed that the intramolecular disulfide Cys[121]-Cys[124] is already present in the product before most of the conversion occurs.

Make-up of the Antigenicity of rHBsAg.

Regarding the ELISA response of rHBsAg product before and after conversion, it could be pictured as a composite of a response towards the Cys[121]-Cys[124] region of the molecule. After the rHBsAg product is converted, additional epitopes are formed by the generation of intermolecular disulfides (and maybe intramolecular as well) and these conformational epitopes resulting from tertiary and quaternary structure arrangement should then be readily detected by an antibody against a truly conformational epitope, e.g., monoclonal H35.

Because of the lack of a true linear relationship between generation of intermolecular disulfides (extent of conversion) and increase in potency, it is believed that that during the last process steps leading to Sterile Filtered Product, (i.e., conversion to form III by KSCN treatment (Wampler et al., 1985)) certain arrays of conformations are acquired with potentially different inter- and intramolecular disulfides links giving rise to different antigenic macrostructures. High ELISA values may then be reached by an optimal oligomerization of individual p24 protein subunits. This oligomerization is likely to comprise several molecular events including (1) approximation of the subunits facilitated by lipid fluidity, (2) formation of inter- and intradisulfides, (3) disulfide exchange or re-shuffling, and (4) final stabilization of the tertiary and quaternary structure. However, the present invention has revealed that rHBsAg with even higher in vitro relative potency values can be made when an optimized folding step is conducted after conversion of the rHBsAg to form III.

Measurement of the Antigenicity and Immunogenicity of rHBsAg.

One can measure the immunogenicity of the rHBsAg product in a variety of ways using in vivo methods currently in use in the art. Those techniques will not in general be described here. However, they can be used to test samples made by the process taught herein. The antigenicity of the rHBsAg product can be assessed by a number of in vitro techniques. The results of these tests can be analyzed to determine the effectiveness of conditions that are varied from those explicitly taught herein as well as to monitor or track the progress of the process as adapted to a particular facility of equipment. The results also provide a foundation for understanding the different effectors and inhibitors of the antigen maturation process. The methodologies as well as examples of the different applications used to study the development of the antigenicity/immunogenicity of the rHBsAg product are discussed below.

While in vivo animal models and in vitro ELISA assays are useful to correlate results with records of how a process was conducted, it can be preferable to monitor the progression of the conformational search in a redox buffer step in as close to real time as possible. It is also preferable to analyze the conformational state of the rHBsAg as it relates to the immunogenicity of the product. Therefore, a method has been employed to monitor the conformational state in real time and the results of that analysis has been correlated to standard immunogenicity tests. The real time method relies on the use of a surface plasmon resonance detector (BIAcore 2000 unit (Upsala, Sweden)). The detector manufactured by BIAcore is preferred, but others can be made or purchased as appropriate. We have correlated the surface plasmon resonance analysis of the conformational state of the rHBsAg by comparison to the widely accepted and commercially available in vitro ELISA assay. The methods of surface plasmon resonance and ELISA assays are described below and the mouse potency assay is described in the Examples.

Standard ELISA Assay for Analysis of rHBsAg Product

Imnunoassays are used to illustrate how the rHBsAg product's structural properties impact the immunogenic response. Examples of various assay values from different Hepatitis B vaccines will be used to illustrate the use of the assay. A standard ELISA assay has about a two day turnaround and multiple sample manipulations needed. This analytical method is useful for process for assessing antigen maturation. The process is advantageously conducted on rHBsAg that has been formulated on an aluminum adjuvant.

Recent scientific publications provide insights into the epitopes recognized by some monoclonal antibodies against rHBsAg (Qui et al., 1996. J Immunol. 156:33350; Chen et al., 1996). The monoclonal H166 would be useful for capture because of its IgM nature (providing multiple Fab binding sites per molecule) and because it recognizes a linear or continuous epitope (Cys[121]-Lys-Thr-Cys[124]) of the rHBsAg (Chen et al.).

The monoclonal H35 is believed to recognize a truly conformational or epitope since it binds to 13 residues located on two discontinuous regions of the rHBsAg molecule (Cys[121] - - - Leu[175]) (Chen et al. 1996). Therefore, this antibody could be conjugated with HRP and used as a reporting antibody to monitor the formation of a conformational epitope.

The amino acid sequences of these epitopes were derived from affinity-enrichment experiments (known as "biopanning") using a filamentous phage display peptide library. (Chen et al. 1996) In addition to biopanning, the site for H166 binding was also determined by cyclic peptide competition (L. Mimms et al. 1989. Second generation assays for the detection of antibody to HBsAg using recombinant DNA-derived HBsAg. J. Viral. Methods 25:211–232.) The presence of a linear "H166 epitope" is also supported by the observation that H166 binds to monomeric p24 in Western blots (L. Mimms et al 1989).

Enzyme immunoassays known in the art can be used to assess the improved rHBsAg. The AUZYME monoclonal enzyme immunoassay, commercially available from Abbott Laboratories, is preferred. To employ the AUZYME assay, one can follow the manufacturer's instructions for a two step procedure. This assay has been found to be quantitative in our hands. Briefly, beads coated with mouse monoclonal antibodies to hepatitis B surface antigen are incubated with the rHBsAg product sample and then with a mouse monoclonal Anti-HBsAg peroxidase conjugate (Anti-HBsAg: HRPO). Unbound material is washed off, and color is developed by adding a 0-phenylenediamine (OPD) solution containing hydrogen peroxide. Development of a yellow-orange color is proportional to the antigen concentration.

Figure 4:
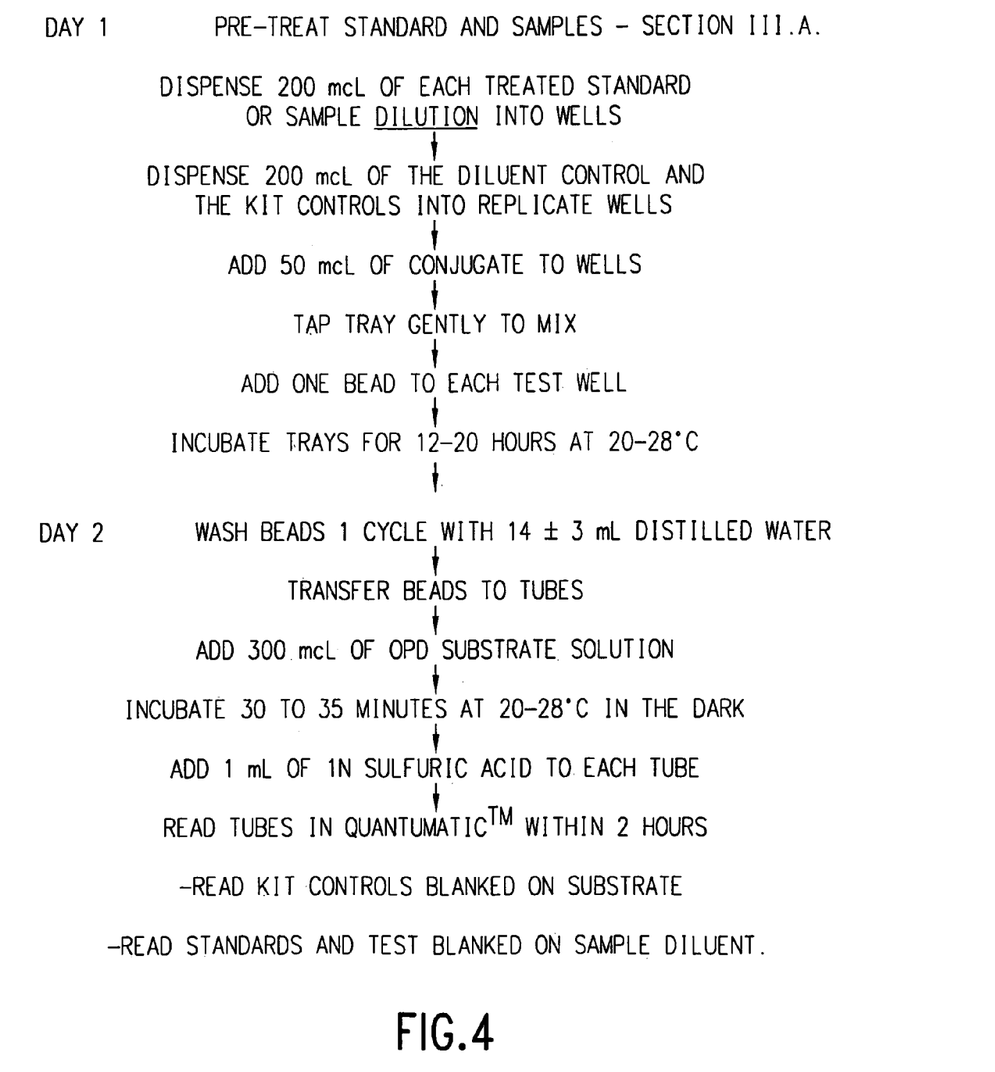
FIG. 4. A flow chart showing the conduct of an ELISA. Vk gene region DNA sequence is SEQ ID NO 3. Vh gene region DNA sequence is SEQ ID NO 4.

The procedure is outlined in greater detail in FIG. 4. It is important to use good testing laboratory technique at each step. After the addition of 1N Sulfuric acid, the absorbencies of the tubes are read in a spectrophotometer at $OD_{492}$.

It is preferable to run serial dilutions of at least 5 levels for each sample so that the resulting data can be analyzed by graphing and samples can be compared at the midpoints of the curves. For example, when the rHBsAg sample is at 5 mcg/ml, the sample should be diluted 1:10, 1:100, 1:500, 1:1000, 1:2000, 1:4000 and 1:8000. Samples from 1:500 to 1:8000 are prepared and tested at least as duplicates or triplicates. For samples at 10 mcg/ml the sample is diluted further to 1:16000 and tested at 1:100–1:16000. For samples at 20 mcg/ml, 30 mcg/ml and 40 mcg/ml dilute to 1:32000, 1:48000 and 1:64000 respectively and duplicates or triplicates are prepared at the appropriate dilutions for testing. These dilutions are exemplary and those of skill in the art can use other appropriate dilutions Diluent controls should be run along with the positive and negative controls provided in the AUZYME kit. The average of three $OD_{492}$ absorbance values for the negative control should be in the range of –0.006 to 0.001. One should then average two at $OD_{492}$ absorbance values for the positive controls and subtract the negative controls from that value. If the resulting value is greater than or equal to 0.400, then the controls are considered valid. The diluent controls should be in the range of at $OD_{492}$ 0+/–0.02. An OPD substrate control can be run and should read less than at $OD_{492}$ 0.006 and –0.100.

One can test the absolute parallelism of the lines derived from the data for each dilution series. It is preferred that the difference in absolute parallelism for a sample is less than 0.17 for the test on that sample to be considered valid. For samples tested on different days, one can test for extravariability. It is preferred that the same samples tested on different days do not vary by more that 1.33 for the test result for a given day to be considered valid.

Herein, the units of measurement for the immunogenicity of a preparation of rHBsAg are grounded in ED50 measured per microgram of protein in the mouse potency assay. However, that assay takes almost two months to generate a result. Therefore, it is preferred to use the ELISA assay taught herein and to correlate the results of that assay to the mouse potency assay. The correlation is monitored by assaying a reference preparation of rHBsAg as a control with each run of the ELISA where the ED50 of the control is known. The correlation was established as follows.

The initial rHBsAg reference material was tested in an in vivo mouse potency model and generated an ED50 value of 0.26 mcg protein. It was decided that the $OD_{492}$ of this material in the in vitro ELISA would be assigned an arbitrary in vitro potency value of 1.0. Thereafter, numerous tests were performed on various batches of rHBsAg in both the ELISA and mouse potency model. Each of the ELISAs were run in parallel with a control rHBsAg sample whose ELISA output was correlated to the ELISA output of the original reference rHBsAg. Because the expected $OD_{492}$ output of the control rHBsAg was known from experience, all ELISA test results could be correlated to the scale established by the original reference rHBsAg. Those values are referred to as in vitro relative potency ("IVRP") values because they are relative to the potency of the original reference rHBsAg in an in vitro ELISA.

Figure 5:
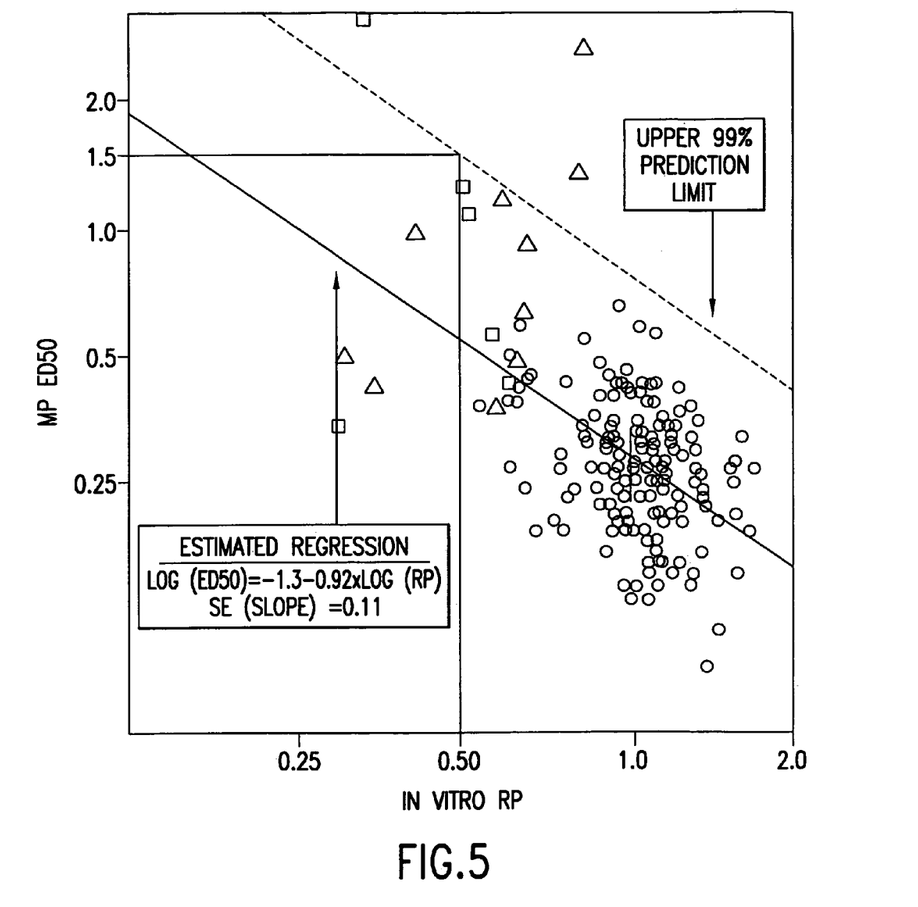
FIG. 5. A graph of the correlation of the antigenicity of rHBsAg measured by ELISA and immunogenicity measured by mouse potency ED50.
Figure 6:
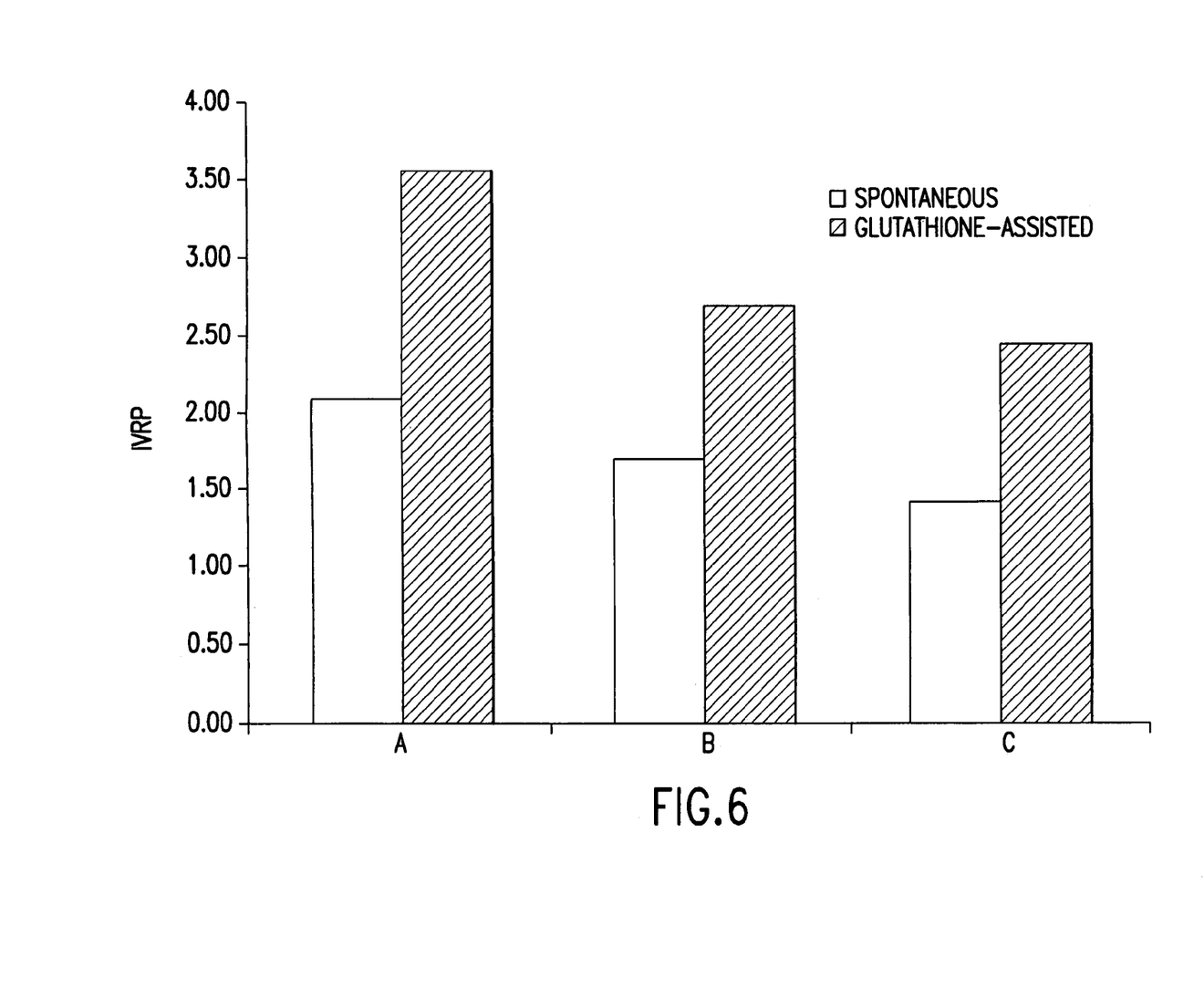
FIG. 6. A graph comparing the ELISA antigenicity of rHBsAg made by using a conformational search step with and without adding a redox buffer.

A graph of in vitro relative potency versus in vivo mouse potency (ED50) is shown in FIG. 5. Each data point represents a sample of rHBsAg that was tested in both the mouse model and by ELISA. These data points were used to generate an equation that related the mouse potency value to the relative potency value obtained by ELISA. Once one has established the correlation of the ED50 and ELISA output scales in this manner, one can now perform ELISA tests and expect to see an ED50 value in line with the output of the regression equation:

$$\text{Log}(ED50)=-1.3-(0.92\times\text{Log}(RP))$$

where Log is natural logarithm and RP is the relative potency obtained by ELISA as outlined above.

ELISA Response of Other Hepatitis B Vaccines

Plasma-derived Dane particles were tested in the ELISA assay. By this method, the Dane particles showed a higher response, of about 5.0. Therefore, the high values for rHBsAg product produced by the present process, i.e., values greater than 2.5, indicates that the rHBsAg particles are approaching an immunogenicity level close to that of the natural product of Hepatitis B virus infection, the Dane particle. However, unlike the Dane particle, particles of HbsAg produced by recombinant methods do not contain Hepatitis DNA.

Surface Plasmon Resonance Assay Using a BIAcore Detector

Like the ELISA assay described above, the BIAcore assay provides quantitative estimate of the rHBsAg's relative immunogenicity under controlled conditions where many factors, such as protein concentrations, temperature, and "contact" time (related to the injection volume and flow rate) among others, are maintained identical for samples and reference. This technique has been used successfully for the epitope mapping of HBsAg (J-S Tung et al. 1998. Characterization of Recombinant Hepatitis B Surface Antigen Using Surface Plasmon Resonance. J. Pharmaceutical Sciences, 87:76–80).

The assay is performed in the following format. Biomolecular interaction assay (BIA) is a technology developed by BIAcore, Inc., for monitoring biomolecular binding in real time. It uses a non-invasive optical detection principle based on surface plasmon resonance (SPR). The SPR response reflects a change of refractive index as a result of mass deposition at a derivatized metallic (gold) sensor surface as molecules bind or dissociate. Because molecules are brought to the surface and the unbound molecules are washed-off by a microfluidic pumping system, the interactions measured are actually binding kinetics. No labeling of the interacting components is required, and the technology is applicable to a wide range of experimental situations.

As in any immunoassay, the proper reagents are important to the method's response and performance. When using the BIAcore technique to monitor the formation of the proper conformation of the improved HBsAg it is most useful to use an antibody that recognizes a conformational epitope. It is also preferable that the antibody binds to an epitope related to the neutralization of the invading hepatitis B virus. An example of such an antibody is a monoclonal antibody called MAb A1.2. It is also believed that the H35 monoclonal antibody of Chen et al 1996 would be appropriate.

The amino acid and DNA sequences of the variable regions of the MAb A1.2 monoclonal antibody were published in Lohman et al., 1993. Molecular Characterization and Structural Modeling of Immunoglobin Variable Regions from Murine Monoclonal Antibodies Specific for Hepatitis B Virus Surface Antigen. Molecular Immunol. 30:1295–1306, and are shown in FIG. C. Using these sequences one can construct an appropriate antibody for use in the surface plasmon resonance assay. Alternatively, from the understanding of the conduct of the assay gained from the descriptions provided herein, one can screen monoclonal antibodies to find one with an appropriate epitope specificity that performs appropriately in the assay.

For analyzing changes in HBsAg antigenicity, the procedure involved the following steps as outlined as follows: (1) chemical immobilization of rat anti-mouse FCgamma on the sensor chip, (2) addition of MAb A1.2 anti-HBsAg which is captured by the rat anti-mouse antibody; and (3) injection of antigen product which is finally captured by MAb A1.2. (4) the antigenicity for the rHBsAg particles is expressed as the ratio between the amount of bound rHBsAg and the amount of bound MAb A1.2. For a normalized protein concentration in compared samples, the difference in the measured binding represents the difference in the HBsAg antigenicity due to the conformation of the rHBsAg. Therefore, by following the increase in the amount of rHBsAg bound in the surface plasmon resonance assay one can monitor the accumulation of rHBsAg having a conformation associated with antigenicity. Thus, one can monitor the incubation step to determine when a given batch of rHBsAg has reached an improved antigenicity. The units used to describe the antigenicity or the rHBsAg are arbitrary and relate only to the control run for the particular assay.

One can perform a series of assays in parallel to measure the response of improved rHBsAg product in a mouse potency model, ELISA and surface plasmon resonance assay. By collecting a series of data points in each assay for different concentrations of a number of preparations of rHBsAg one can generate a date set useful to correlate the responses obtained from an ELISA, the surface plasmon resonance assay and the mouse potency assay. Once one has gained sufficient experience in these assays one can rely predominantly on the ELISA to for general monitoring of the antigenicity of the rHBsAg product. One can also rely on the surface plasmon resonance assay to monitor the progress of a folding step while making the product and to gauge when the product is achieving a high level of conformationally dependent antigenicity.

Improved rHBsAg in Vaccines

Vaccines including HBsAg from plasma and rHBsAg expressed in a variety of host cells (e.g., insect, yeast, mammalian cells including CHO cells) are in common use in the art. The improved rHBsAg of this invention can be made by adding the redox step to the present processes used to make rHBsAg from the various host cells. Thereafter, the improved rHBsAg can be used to make any of the vaccines in which the presently made rHBsAg is used. As these vaccines and their preparation are known in the art they will not be described here other than by name: RECOMBIVAX HB, ENERGIX, COMVAX, PRIMIAVAX, PENTAVAX, & TWINRIX.

It will also be recognized by practitioners in the art that pharmaceutically useful compositions comprising the improved rHBsAg can be formulated according to known methods such as by the admixture of a pharmaceutically acceptable carrier. The improved rHBsAg can be adjuvanted and formulated using the usual practices of the pharmaceutical arts as exemplified by practice manuals and texts including Remington's Pharmaceutical Sciences. To form a pharmaceutically acceptable composition suitable for effective administration, such compositions will contain an effective amount of the improved rHBsAg.

Particular compositions can be made by adjuvanting the improved rHBsAg. Many adjuvants are known in the art. Aluminum adjuvants are frequently used because they are presently approved for use in human patients. Aluminum adjuvants can be provided as amorphous or crystalline forms. Common aluminum adjuvants include aluminum phosphate, aluminum hydroxide, and aluminum hydroxyphosphate. All of these can be used with the improved rHBsAg.

Common methods of adjuvanting used in the art can be applied to the improved rHBsAg and include co-precipitation of the adjuvant and rHBsAg and adsorption of the rHBsAg onto the adjuvant. Other adjuvants can be used and include saponins, lipids including cationic lipids, oligonucleotides having a CpG motif, muramyl dipeptides and DNA vaccines (Donnelly, J. J., Friedman, A., Deck, R. R., DeWitt, C. M., Caulfield, M. J., Liu, M. A., and Ulmer, J. B. 1997. Adjuvant effects of DNA vaccines. In *Vaccines* 97. F. Brown, F. Burton, P. Doherty, J. Mekalanos, and E. Norrby, eds. Cold Spring Harbor Laboratory Press, Cold Spring Harbor, N.Y., p. 105–111).

Therapeutic or prophylactic vaccines according to this invention include the improved rHBsAg and are administered to an individual in amounts sufficient to treat or prevent disorders associated with infection by hepatitis virus. Advantageously, vaccines of the present invention can be administered in a single dose, or the total dosage can be administered in divided doses of two, three or more doses over a period of time as determined to by effective by a skilled physician. The number of doses will be influenced by whether the rHBsAg containing vaccine is being administered for prophylactic or therapeutic treatment of a patient.

The dosage amount and regimen utilizing vaccines that include the improved rHBsAg of the present invention are selected in accordance with a variety of factors including type, species, age, weight, sex and medical condition of the patient; the severity of the condition to be treated; the route of administration; the renal, hepatic and cardiovascular function of the patient; and the particular vaccine employed. A physician or veterinarian of ordinary skill can readily determine and prescribe the effective amount of the drug required to prevent, counter or arrest the progress of the condition and determine an appropriate dosage regimen.

For combination vaccines with more than one active immunogen, where the active immunogens can be in separate dosage formulations, they can be administered concurrently, or they each can be administered at separately staggered times. For cases of concurrent administration, improved rHBsAg can be formulated in a combination vaccine with other active immunogens. For example, the improved rHBsAg can be formulated with immunogens such as, and without limitation, *Hemophilus influenza* polyribitol phosphate that has been conjugated to a toxoid or a protein such as the outer membrane protein complex of *Neiserria meningitis*; Measles, Mumps and Rubella immunogens; Diptheria toxoid; Tetanus toxoid; Pertussis, either whole cell or a-cellular [a-cellular meaning at least one of the following Pertussis immunogens: Pertussis Toxoid (also called Lymphocytosis Promoting Factor), Filimentous Hemagglutinin, 69 kd Protein (also called Pertactin), Agglutinogen 2 and Agglutinogen 3]; inactivated or attenuated live *Varicella zoster; Streptococcus pneumonia* capsular polysaccharide conjugated to a toxoid or a protein such as *Neiserria menningitis* outer membrane protein complex; inactivated or attenuated Polio virus; inactivated or attenuated Rabies virus; Lyme disease immunogens; and Hepatitis A virus that has been inactivated, attenuated or attenuated and inactivated. Finally, the rHBsAg can be formulated with a DNA vaccine(s) encoding an immunogen(s) alone or in addition to other immunogens listed above.

An advantage of a vaccine formulated with the improved rHBsAg is that one can use a lower amount of the immunogen and achieve the same efficacy as the vaccines presently available in the art. An additional advantage is that one can formulate a vaccine that includes an amount of improved rHBsAg equal to an amounts used in present formulations and produce a stronger response in a patient.

The following examples are presented by the way of illustration and, because various other embodiments will be apparent to those in the art, the following is not to be construed as a limitation on the scope of the invention.

EXAMPLE 1

Method of Making Improved Recombinant Hepatitis B Surface Antigen

This embodiment of the method will be described on a lab scale. However, it will be understood by those skilled in the art that the process can be scaled as appropriate.

Sterile filtered product (SFP) in phosphate buffered saline (6 mM phosphate, 0.15 M NaCl) was manufactured as known in the art (Wampler 1985) and stored at 4° C. Thereafter, to a solution of 200 mL SFP in a Pyrex glass bottle, glutathione (GSH) and oxidized glutathione (GSSG) were introduced to the final concentrations of 1.0 mM and 0.2 mM, respectively. Once the mixing was completed, the batch temperature was ramped up to 37° C. in an incubator.

Once temperature was reached, the batch was incubated for 44 hrs. An amount of 300 mM formaldehyde solution, equivalent to 0.01 times the batch weight, was introduced, resulting a final concentration of 3 mM formaldehyde. After the formalin was added the batch was mixed gently for about 5 minutes to disperse the formalin.

After the agitation was concluded the batch was incubated further for another 60 hrs. It is preferable that the total time from the beginning of the heating step through the end of this incubation should be between 100 to 105 hours. At the end of that time period the batch is cooled to 2–8° C. without mixing.

When batch temperature reaches 2–8° C., agitation was begun and (5.44%) potassium aluminum sulfate solution was added to the aqueous rHBsAg solution. The adjuvanted product was precipitate by adding 1 N NaOH. The product was washed by settle/decant washes with 0.15 M NaCl, 6 times. 1.4% Sodium Borate was added to resuspend the rHBsAg to the same concentration as when it started. We refer to this product as Bulk Alum Product (BAP). BAPs were tested in the in vitro relative potency assay.

In vitro relative potency values of more than 3.0 can be obtained. In vitro relative potency values can be expected to range from about 2.5 to about 4.0, more usually, from about 2.75 to about 3.5 or 3.75, and commonly from about 2.75 or 3.0 to about 3.25 or 3.5. Higher values can also be achieved if the formalin step is omitted. In that case, values can range as above and up to about 4.25, 4.5, 4.75, 5.0, 5.25, 5.5, 5.75 or 6.0.

It should be noted that the incubation in the presence of GSH/GSSG in this Example was conducted for 44 hours but the incubation can be conducted longer as described above. An incubation of about 100 hours can be preferable to one of 40 hours. However, while one can incubate for less than 40 hours, at least 40 hours is preferred.

EXAMPLE 2

Measurement of Antigenicity of Recombinant Hepatitis B Surface Antigen in vivo

An accepted measurement of the immunogenicity of rHBsAg which will lead to an appropriate immune response in an animal is the efficacy of rHBsAg in a live mouse model. The assay is conducted to measure the dose of a preparation of rHBsAg that is effective in producing an immune response in the animal. This test is sometimes referred to in the art as a mouse potency test.

The mouse potency (MP) test is performed by preparing a series of 2-fold dilutions of the rHBsAg product using the adjuvant solutions (1×Alum with antigen, other components are the same with rHBsAg preparations) are injected into adult Balb/C mice. An appropriate format is to use five groups of eight mice. Each group is tested at one of five concentrations of rHBsAg, e.g. 1.0 mcg/mL to 0.0625 mcg/mL. As one gains experience with the assay it is preferable to provide dilutions such that the projected ED50 is about in the in the middle of the test range. After injection, the mice are held for 6 weeks, bled and the individual sera are tested for anti-HBsAg using "AUSAB-EIA" diagnostic kit (Abbott Lab) following the manufacturer's instructions to determine the immuno-response by measuring the total anti-HBsAg B antibodies. The potency of the rHBsAg is reported as the dose which elicits antibody response in 50% of the mice (ED50).

EXAMPLE 3

Spontaneous Versus Redox Buffer Assisted Refolding

To control for process parameters unrelated to the use of a redox buffer to make an improved rHBsAg, three experiments were conducted in which sterile filtered product was processed in parallel with and without the addition of the redox buffer. The process used was as described in Example 1. The incubation in the presence and absence of redox buffer was conducted at 36° C. for 40 hours. Thereafter, the rHBsAg products were tested in the in vitro relative potency ELISA assay. The data is presented in the table below and graphed in FIG. 6.

| | | IVRP |
|---|---|---|
| A | (−) | 2.09 |
| | (+) | 3.56 |
| B | (−) | 1.69 |
| | (+) | 2.70 |
| C | (−) | 1.44 |
| | (+) | 2.47 |

All the experiments were done under identical conditions except that in the (+) arms 1.0 mM GSH and 0.2 mM GSSG were included during incubation at 37° C. All the samples in the same group (A, B or C) were tested side by side under the same conditions.

EXAMPLE 4

Correlation of MAb A1.2 Affinity in Aqueous Solutions and IVRP of Final Liquid (FAP) and Formulated Products (BAPs)

The in vitro relative potency, in vivo mouse potency and clinical performance of bulk alum formulated rHBsAg can be monitored by appropriate tests as taught herein or as are in practice in the art. However, when conducting the process to make the rHBsAg, it is preferable to have a tool to measure the progress of the production of conformationally active rHBsAg in a liquid, non-adjuvanted sample without having to wait the days or weeks necessary for ELISA or in vivo methods to report a meaningful measurement.

The surface plasmon resonance (SPR) technology embodied in the BIAcore equipment is useful for monitoring the real time maturation of conformationally appropriate rHBsAg. This Example describes how to use the technology by correlating the SPR measurement of a liquid sample taken during a process step and to a reference standard of rHBsAg.

The binding surface of the SPR detector is made of a derivatized metal, preferably gold. In this Example, a rat anti-mouse FCgamma is covalently coupled to the derivatized gold surface through an amine coupling. Then a mouse anti-rHBsAg monoclonal antibody that binds to a conformational epitope is contacted with the detector and bound to the surface by the rat anti-mouse antibody. The detector surface is then washed with a buffer appropriate to the binding of the rHBsAg by the mouse monoclonal antibody.

It is important to use an antibody that binds a conformational epitope. Techniques for testing an antibody for binding to a conformational epitope are known. Several antibodies that bind conformational epitopes of rHBsAg are also known and include H35 (Chen et al., 1996) and MAb A1.2 (Lohman et al., 1993). The MAb A1.2 antibody is the preferred antibody.

The detector is calibrated by binding a reference standard of rHBsAg for which the in vitro relative potency of the product formulated on alum is known. Because the SPR technology is used to measure non-adjuvanted material in a liquid system, reference rHBsAg material needs to be preserved in a non-adjuvanted form, preferably as sterile filtered product.

The detector is calibrated by binding a reference standard of rHBsAg. Because the SPR technology is used to measure non-adjuvanted material in a liquid system, reference rHBsAg material needs to be preserved in a non-adjuvanted form, preferably as final aqueous product. It has been found that a reference standard of FAP (final aqueous product) can be stored at 4° C. for over two years. The reference should be aged for at least six months and preferably aged over 2 years. The technique is conducted according to the manufacturer's directions or as described in the literature (Tung et al (1998) J. Pharm. Sci. 87, 76–80 (1998); (Biacore AB, Sweden, BIACORE® 2000 Instrument Handbook and BIA applications Handbook, 1996). Ethanolamine-HCl, NHS (N-Hydroxysuccinimide) and EDC (N-Ethyl-N'-(3-dimethylaminopropyl)-carbodiimide hydrochloride) reagents were obtained from the manufacturer (BIAcore) and used according to directions. Sample and calibration standards are diluted to 11 mcg/ml in prepared in 0.15 mM NaCl, 6 mM phosphate, and TWEEN 20 is added to 0.05%.

1) Coupling antibody: rat-anti-mouse Fcg (BIAcore, Inc.) 50 μg/mL in 10 mM sodium acetate buffer pH 4.8 is immobilized on the surface of sensor chip through amine coupling using the Ethanolamine-HCl reagent.
2) Binding monoclonal antibody: (e.g. Mab A1.2 purified at 1.0 mg/ml, and diluted 20-fold to 50 μg/ml using HBS buffer (10 mM HEPES, 0.15 mM NaCl, 3 mM EDTA, 0.005% TWEEN 20, pH 7.4 filtered and degassed) (Biacore) prior to assay.) is then injected and immobilized;
3) Antigen binding: rHBsAg in solutions is injected and certain amount of antigen will be immobilized by specific antigen-antibody interactions;
4) Regeneration: The surface of the detector is exposed briefly to acid (e.g. 20 mM HCl/10 mM aspartic acid/1% TWEEN 20) to remove the non-covalently-immobilized monoclonal antibody and antigen to regenerate the surface for the next cycle of assay;
5) The ratio between the amount of antigen vs. monoclonal antibody is used to represent the antigenicity of the tested aqueous preparations of rHBsAg.

The 68 data points were accumulated during a period of several months. The relative antigenicity of final aqueous products at 11 mcg/ml was measured against a reference standard at the same concentration. The Mab A1.2 binding to rHBsAg was carried out at 20° C. in 6 mM potassium phosphate and 0.15 M NaCl. However, during the assay the sampling block is cooled to about 10° C. Between assay cycles, the detector surface is briefly exposed to acid to remove the non-covalently-immobilized monoclonal antibody and antigen to regenerate the surface for the next cycle of assay. The antigenicity is expressed as the ratio between the amount of rHBsAg and the amount of Mab A1.2 bound to the sensor chip surface. Then, this ratio was normalized to the ratio for the calibration standard. After the formulation with adjuvant, ELISA was carried out on the corresponding bulk Alum products and IVRP values were derived. Good correlation between Mab A1.2 binding of rHBsAg by SPR and the IVRP by conventional ELISA as shown in FIG. 7.

In this Example, a total of sixty eight data points were collected. Each data point represents a sample for which the in vitro relative potency of the alum formulated rHBsAg product was determined and compared to a surface plasmon resonance measurement of the liquid non-adjuvanted rHBsAg product. From these data points, a linear fit yielded the theoretical line and parameters shown in FIG. 7. The figure shows the linear relationship between IVRP of product formulated on alum versus the relative antigenicity of the rHBsAg in final aqueous form as a (%) of a reference standard as measured by SPR.

Figure 7:
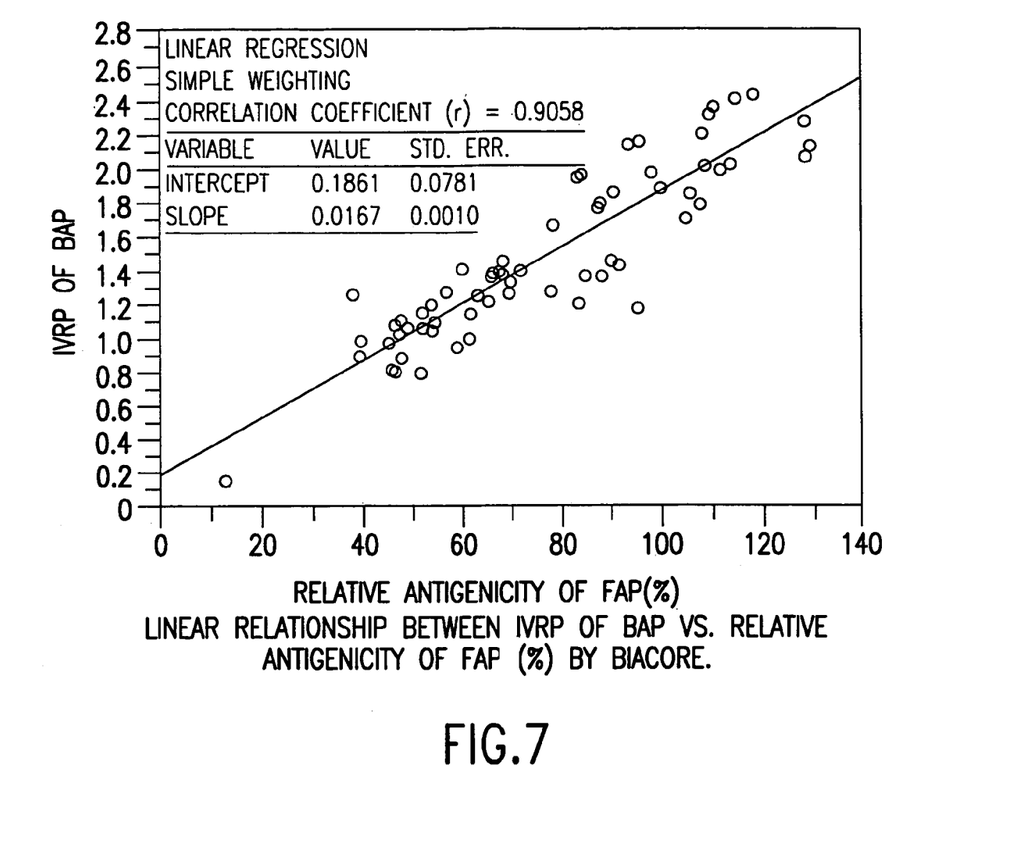
FIG. 7. A graph of in vitro relative potency (IVRP) versus the relative antigenicity measured by surface plasmon resonance.

The SPR measurements of the liquid form of the rHBsAg product correlate well with the in vitro relative potency values obtained once the rHBsAg product is adjuvanted with alum. Therefore, the SPR technology can be used to monitor the real-time formation of conformational epitopes whose presence in the rHBsAg product result in antigenicity in vitro and immunogenicity in vivo.

EXAMPLE 5

Conformational Maturation Using a Redox Buffer Including Thiol Compounds

Various concentrations and ratios of reduced and oxidized thiol compounds can be used in the redox buffer folding step. We prefer the use of glutathione (GSH) and oxidized glutathione (GSSG). In this Example, various levels of GSH and GSSH were tested in the procedure of Example 1.

All steps began by providing a liquid sterile filtered rHBsAg product made, e.g., by the method of Wampler et al. (1985). The thiol compounds were added, the liquid was mixed briefly and was warmed to between about 34° C. to about 38° C. and usually about 36° C. The liquid was held without agitation. Samples were taken at various times and compared to a reference rHBsAg standard by surface plasmon resonance measurements.

As would be recognized in the art, a diafiltration step can be added after the incubation, if desired, to remove the residual redox buffer agents from the rHBsAg.

FIG. 2A shows that there is a synergistic effect when GSH and GSSG are combined in a redox buffer. FIG. 2B shows that there is an increase in the amount of rHBsAg containing important conformational epitopes as the amount of GSH alone is increased.

EXAMPLE 6

Experiments with and without Formalin

Three laboratory scale batches of rHBsAg were prepared according to the method of Example 1. In Batch A, the formalin step was included while in Batches B and C formalin was omitted. The redox incubation was performed in a glass tank for Batches A and B and in a stainless steel tank for Batch C. The control batch was made without the redox buffer, with formalin and conducted in a glass tank. The length of the incubation step was not optimized for any of the batches.

| Batch   | IVRP | $ED_{50}$    |
|---------|------|--------------|
| Control | 2.51 | 0.15, 0.13   |
| Batch A | 4.32 | 0.074, 0.125 |
| Batch B | 4.62 | 0.088, 0.0725|
| Batch C | 4.30 | 0.087, 0.13  |

The ELISA based IVRP and mouse $ED_{50}$ results demonstrate that the rHBsAg produced by the method of this invention has very high antigenicity and immunogenicity. If the above data is compared to the historical data for rHBsAg made by prior art methods shown in FIG. 5., the present data plots lower and to the right of the historical data.

What is claimed:

1. A method of increasing the antigenicity of recombinant hepatitis B surface antigen (rHBsAg) comprising:
   a) providing soluble sterile filtered rHBsAg purified from a cell culture,
   b) adding a redox buffer to the rHBsAg,
   c) adjusting the temperature to 34 to 38° C.,
   d) incubating the rHBsAg at 34 to 38° C. for 40 to 240 hours, wherein the antigenicity of the rHBsAg produced after step d is greated than the antigenicity of the rHBsAg provided in step a.

2. The method of claim 1 wherein step c is performed before step b.

3. The method according to claim 1 wherein the redox buffer comprises thiol compounds selected from the group consisting of thiol compounds having a MW less than about 1000 Da and the corresponding disulfide compounds.

4. The method according to claim 3 wherein the redox buffer is a mixture of at least one thiol compound and at least one disulfide compound.

5. The method according to claim 4, wherein the ratio of thiol compound to disulfide compound is between about 30:1 and about 1:1.

6. The method according to claim 5 wherein the concentration of thiol compound is between about 0.05 mM and about 5.00 mM.

7. The method according to claim 6 wherein the ratio of thiol to disulfide is selected from the group consisting of about 20:1, about 10:1, about 10:4, about 5:1, about 2:1 and about 1:1.

8. The method according to claim 6 wherein the thiol compound is glutathione and the disulfide compound is oxidized glutathione.

9. The method according to claim 8 wherein the concentration of glutathione is about 1.0 mM and the concentration of oxidized glutathione is about 0.2 mM.

10. The method according to claim 1 further comprising the steps of e) adding an aluminum adjuvant, and f) co-precipitating the rHBsAg and the adjuvant.

11. The method according to claim 1 further comprising the steps of e) adding about 0.01% final concentration of formalin, f) incubating the rHBsAg at from about 34° C. to about 38° C. from about 40 to about 72 hours, wherein the incubation in step d is from about 40 to about 190 hours.

12. The method according to claim 11 further comprising the steps of g) adding an aluminum adjuvant, and h) co-precipitating the rHBsAg and the adjuvant.

13. The method according to claim 1 wherein the incubation in step d is about 60 hours and further comprising the steps of e) adding an aluminum adjuvant, and f) co-precipitating the rHBsAg and the adjuvant, wherein step f includes an incubation of about 40 hours.

* * * * *